(12) United States Patent
Nakano et al.

(10) Patent No.: US 11,373,300 B2
(45) Date of Patent: Jun. 28, 2022

(54) IMAGE STITCHING USING GEOMETRY-BASED IMAGE ORIENTATION

(71) Applicant: International Business Machines Corporation, Armonk, NY (US)

(72) Inventors: Hiroki Nakano, Otsu (JP); Yoshinori Kabeya, Kawasaki (JP); Sho Yonezawa, Kashiwa (JP); Haruka Ichimura, Kodaira (JP); Tomoko Murayama, Yokohama (JP)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/779,124

(22) Filed: Jan. 31, 2020

(65) Prior Publication Data
US 2021/0241451 A1  Aug. 5, 2021

(51) Int. Cl.
*G06T 7/00* (2017.01)
*A61B 5/00* (2006.01)

(52) U.S. Cl.
CPC ............ *G06T 7/0012* (2013.01); *A61B 5/445* (2013.01); *G06T 2207/10056* (2013.01); *G06T 2207/20212* (2013.01); *G06T 2207/30088* (2013.01)

(58) Field of Classification Search
None
See application file for complete search history.

(56) References Cited

U.S. PATENT DOCUMENTS

| 8,428,335 | B2 * | 4/2013 | Ge ............................ G06T 7/12 382/141 |
| 9,739,783 | B1 * | 8/2017 | Kumar ............. G01N 33/57415 |
| 9,955,900 | B2 | 5/2018 | O'Connor et al. |
| 10,403,240 | B2 | 9/2019 | Yamane |
| 2018/0028065 | A1 * | 2/2018 | Elbaz ...................... G06T 17/00 |

(Continued)

FOREIGN PATENT DOCUMENTS

| CN | 107507208 A | * | 12/2017 |
| JP | 2003535514 A | | 11/2003 |
| WO | WO-2015165222 A1 | * | 11/2015 ............... G06T 5/50 |

OTHER PUBLICATIONS

Machine translation of WO-2015165222-A1 (Year: 2015).*

(Continued)

*Primary Examiner* — Vu Le
*Assistant Examiner* — Courtney Joan Nelson
(74) *Attorney, Agent, or Firm* — Garg Law Firm, PLLC; Rakesh Garg; Michael O'Keefe (57) ABSTRACT

Within a first image in a set of images comprising a panoramic view of a scene, a first boundary feature is identified using a model. Within the first boundary feature, a first set of points is selected. Within a second image in the set of images, a second boundary feature is identified using the model. Within the second boundary feature, a second set of points is selected. A set of parameters of a geometrical shape including the first set of points and the second set of points is determined. From the first image and the second image, a panoramic image is formed, the first image placed within the panoramic image according to the position of the first image on the geometrical shape, the second image placed in the panoramic image according to the position of the second image on the geometrical shape.

17 Claims, 9 Drawing Sheets

(56) References Cited

U.S. PATENT DOCUMENTS

2018/0082401 A1* 3/2018 Bai ................. G06T 11/60
2018/0289977 A1 10/2018 Fishman

OTHER PUBLICATIONS

Machine translation of CN-107507208-A (Year: 2017).*
Allen et al., Image Analysis of Nailfold Capillary Patterns from Video Sequences, MICCAl'99, LNCS 1679, 1999, pp. 698-705.
Ronneberger et al., U-Net: Convolutional Networks for Biomedical Image Segmentation, Medical Image Computing and Computer-Assisted Intervention (MICCAI), Springer, LNCS, 2015, vol. 9351, pp. 234-241, http://lmb.informatik.uni-freiburg.de/people/ronneber/u-net.

* cited by examiner

IMAGE STITCHING USING GEOMETRY-BASED IMAGE ORIENTATION

TECHNICAL FIELD

The present invention relates generally to a method, system, and computer program product for image stitching for panoramic images. More particularly, the present invention relates to a method, system, and computer program product for image stitching using geometry-based image orientation.

BACKGROUND

A panoramic image is a wide-angle representation of a physical scene or object. A panoramic image is typically assembled from a set of other-than-wide-angle images. One example method of generating a panoramic image is to use a camera with a standard-angle (not a wide-angle) lens to generate a series of images of a subject, moving the camera a specified amount between generating each image so as to obtain a set of images of portions of the subject, then assemble the set of standard-angle images into one panoramic image. Image stitching is the process of combining multiple images with different fields of view to produce a segmented panoramic image.

One example use case for image stitching involves dermatology, in which diagnosis of the progress of a disease called collagen disease involves observation of blood capillaries at a boundary between fingernail and skin using a close-up microscope with a magnification of about 200×. To allow a doctor's evaluation of the shape and abnormality of the blood capillaries, a set of about 10 still images of a patient's fingernail region are taken and the still images stitched together to create one panoramic image of the region. Other use cases, both within the field of medical imaging and in other fields of endeavor, are also contemplated.

SUMMARY

The illustrative embodiments provide a method, system, and computer program product. An embodiment includes a method that identifies, within a first image in a set of images using a model, a first boundary feature, wherein the set of images comprises a panoramic view of a scene. An embodiment selects, within the first boundary feature, a first set of points. An embodiment identifies, within a second image in the set of images using the model, a second boundary feature. An embodiment selects, within the second boundary feature, a second set of points. An embodiment determines a set of parameters of a geometrical shape, the geometrical shape including the first set of points and the second set of points. An embodiment forms, from the first image and the second image, a panoramic image, the first image placed within the panoramic image according to the position of the first image on the geometrical shape, the second image placed in the panoramic image according to the position of the second image on the geometrical shape.

An embodiment includes a computer usable program product. The computer usable program product includes one or more computer-readable storage devices, and program instructions stored on at least one of the one or more storage devices.

An embodiment includes a computer system. The computer system includes one or more processors, one or more computer-readable memories, and one or more computer-readable storage devices, and program instructions stored on at least one of the one or more storage devices for execution by at least one of the one or more processors via at least one of the one or more memories.

BRIEF DESCRIPTION OF THE DRAWINGS

Certain novel features believed characteristic of the invention are set forth in the appended claims. The invention itself, however, as well as a preferred mode of use, further objectives and advantages thereof, will best be understood by reference to the following detailed description of the illustrative embodiments when read in conjunction with the accompanying drawings, wherein:

DETAILED DESCRIPTION

The illustrative embodiments recognize that image-stitching can be performed manually. However, manual image stitching is time-consuming. In addition, in specialized uses such as medical imaging, image stitching is often performed by the medical professional evaluating a set of images, taking time from that professional's other medical duties. Thus, manual methods are impractical when more than a few sets of images are to be processed As well, there are likely to be variations between panoramic images when different individuals perform image stitching, and these variations are undesirable.

The illustrative embodiments recognize that presently-available automatic image-stitching methods require that images to be stitched together share a common region. Given a set of images to be stitched together, presently-available feature-based methods such as scale-invariant feature transform (SIFT), Principal Component Analysis SIFT (PCA-SIFT), Bag of Features (BOF), Features from Accelerated Segment Test (FAST), Speed-up Robust Feature detector (SURF), and Oriented FAST and Rotated BRIEF (ORB) match features extracted from input images against each other, then use the matched features to determine overlap regions between images, arrange the images using the overlap regions, and combine the images into a panoramic image. Feature-based methods are typically insensitive to one or more of the ordering, orientation, scale and illumination of the source images, but do require that there be sufficient overlap between images with which to match features.

The illustrative embodiments recognize that insufficient overlap between images can arise in at least two ways. First, when imaging a static scene, reorienting the camera with too great a change between source images, especially when reorienting the camera both horizontally and vertically, can result in insufficient or no overlap between images—in other words, the source images are discontinuous. Discontinuous source images can occur, for example, when tracking a moving object, because of the camera movement necessary to keep the moving object within the camera's field of view. Second, when imaging a scene with elements that change while the set of images is being generated, even two images of the same portion of the scene may be too different to identify common features. For example, when generating panoramic images of human skin, capillaries under the skin surface can change while the set of images is being generated, preventing identification of common features. As another example, when generating panoramic images of a fast-moving object against a background of trees, wind blowing the tree leaves while the set of images is being generated can also prevent identification of common features. Thus, the illustrative embodiments recognize that there is an unmet need to automatically generate panoramic images using image stitching when the source images are discontinuous or common features in the source images cannot be identified for other reasons.

The illustrative embodiments recognize that the presently available tools or solutions do not address these needs or provide adequate solutions for these needs. The illustrative embodiments used to describe the invention generally address and solve the above-described problems and other problems related to image stitching using geometry-based image orientation.

An embodiment can be implemented as a software application. The application implementing an embodiment can be configured as a modification of an existing image stitching system, as a separate application that operates in conjunction with an existing image stitching system, a standalone application, or some combination thereof.

Particularly, some illustrative embodiments provide a method that identifies a boundary feature in images and points within the boundary feature. The method determines a set of parameters for a geometrical shape that includes the points, and places the images into a panoramic image according to the points' placement on the geometrical shape.

An embodiment receives a set of source images of a subject or scene from which to form a panoramic image. In one embodiment, the set of images is arranged in order of appearance in the scene. In another embodiment, the set of images is arranged randomly. In another embodiment, the set of images is arranged in a different order. Images in the set of images may have been obtained individually, as still images, or may be individual frames extracted from a video segment.

An embodiment identifies a boundary feature in a source image. A boundary feature separates two areas in the scene portrayed in the set of source images. Thus, the identified boundary feature should be present in each source image. For example, when the set of images is a set of nail scan images portraying portions of a human fingernail and surrounding skin, one identifiable boundary feature is the cuticle, a narrow region following the contour of the nail and separating the nail region from the surrounding skin.

To identify a boundary feature, an embodiment uses a model trained to identify boundary features in images of a type the embodiment is configured to process. One embodiment uses U-Net, a presently-available fully convolutional network that performs image segmentation, thereby identifying a boundary feature as a smooth contour between image segments. One embodiment trains the model using a set of training images, with boundary features annotated by a human expert. For example, when training for processing nail scan images, the training set is a set of nail scan images, each with a boundary feature (e.g. the cuticle region) annotated by a human medical professional or other expert. Once trained to process nail scan images, the model can be used to identify boundary features in unannotated nail scan images.

An embodiment treats an identified boundary feature within an image as a line segment, and selects a set of points within the line segment. One embodiment selects three points, at ten percent, fifty percent, and ninety percent of the length of the line segment. Other numbers of points, at other locations along the line segment, are also possible and contemplated within the scope of the illustrative embodiments. In addition, the set of points need not be evenly spaced along the line segment.

An embodiment determines a set of parameters for a geometrical shape that includes the identified points within a source image. In other words, an embodiment fits a geometrical shape to the identified points. In one embodiment, the geometrical shape is a circle, and for each selected point with coordinates x and y in the source image the embodiment calculates a radius r of the circle defined by the expression $(x-x_0)^2+(y-y_0)^2=r^2$ with fixed center coordinates $x_0$ and $y_0$. The embodiment then averages all the radii. For example, fitting the sets of points to a circle is well-suited to processing nail scan images. In another embodiment, the geometrical shape is an ellipse, and for each selected point with coordinates x and y in the source image the embodiment calculates parameters of an ellipse passing through x and y. In another embodiment, the geometrical shape is a parabola. For example, fitting sets of points to a parabolic arc is well-suited to processing images tracking a parabolic trajectory of an object such as a golf ball. Other geometrical shapes, appropriate to the type of source image being processed, are also possible and contemplated within the scope of the illustrative embodiments.

An embodiment performs the boundary feature identification, point selection, and parameter determination for additional images in the set of source images, averaging the parameters. Thus, an embodiment fits an identified boundary feature within multiple source images to a common geometrical shape.

An embodiment uses the determined parameters of the common geometrical shape to arrange images in the set of source images in positions along the geometrical shape. For an embodiment using a circle as the common geometrical shape, the embodiment calculates a phase for each identified point within an image. The phase represents a distance around the arc of the circle from a starting point. The embodiment uses the calculated phases in images in the set of source images to position the source images appropriately. For example, if source image one includes points at −20, −15, and −10 degrees, source image two includes points at −5, 0, and +5 degrees, and source image three includes points at +10, +15, and +20 degrees, image two belongs in the center of the resulting panoramic image, with image one at one side and image three at the other side.

An embodiment forms a panoramic image by combining the positioned source images. An embodiment uses any presently-available image-combining technique to combine the positioned source images. If there is an overlap between a portion of a positioned source image and a portion of an adjacent source image, an embodiment selects one of the source images for use in the panoramic image according to a selection criterion. In embodiments, the selection criterion is an image quality criterion or an overlap region size criterion, or a combination. Another embodiment combines the two images in the overlap region, using any suitable image combination technique. Another embodiment preserves both images contributing to the overlap, allowing a user to select which image of the overlap region is to be used.

The manner of image stitching using geometry-based image orientation described herein is unavailable in the presently available methods in the technological field of endeavor pertaining to image stitching. A method of an embodiment described herein, when implemented to execute on a device or data processing system, comprises substantial advancement of the functionality of that device or data processing system in identifying a boundary feature in images and points within the boundary feature. The method determines a set of parameters for a geometrical shape that includes the points, and places the images into a panoramic image according to the points' placement on the geometrical shape.

The illustrative embodiments are described with respect to certain types of source images, panoramic images, geometrical shapes, geometrical parameters, boundary features, models, positionings, arrangements, devices, data processing systems, environments, components, and applications only as examples. Any specific manifestations of these and other similar artifacts are not intended to be limiting to the invention. Any suitable manifestation of these and other similar artifacts can be selected within the scope of the illustrative embodiments.

Furthermore, the illustrative embodiments may be implemented with respect to any type of data, data source, or access to a data source over a data network. Any type of data storage device may provide the data to an embodiment of the invention, either locally at a data processing system or over a data network, within the scope of the invention. Where an embodiment is described using a mobile device, any type of data storage device suitable for use with the mobile device may provide the data to such embodiment, either locally at the mobile device or over a data network, within the scope of the illustrative embodiments.

The illustrative embodiments are described using specific code, designs, architectures, protocols, layouts, schematics, and tools only as examples and are not limiting to the illustrative embodiments. Furthermore, the illustrative embodiments are described in some instances using particular software, tools, and data processing environments only as an example for the clarity of the description. The illustrative embodiments may be used in conjunction with other comparable or similarly purposed structures, systems, applications, or architectures. For example, other comparable mobile devices, structures, systems, applications, or architectures therefor, may be used in conjunction with such embodiment of the invention within the scope of the invention. An illustrative embodiment may be implemented in hardware, software, or a combination thereof.

The examples in this disclosure are used only for the clarity of the description and are not limiting to the illustrative embodiments. Additional data, operations, actions, tasks, activities, and manipulations will be conceivable from this disclosure and the same are contemplated within the scope of the illustrative embodiments.

Any advantages listed herein are only examples and are not intended to be limiting to the illustrative embodiments. Additional or different advantages may be realized by specific illustrative embodiments. Furthermore, a particular illustrative embodiment may have some, all, or none of the advantages listed above.

Figure 1:
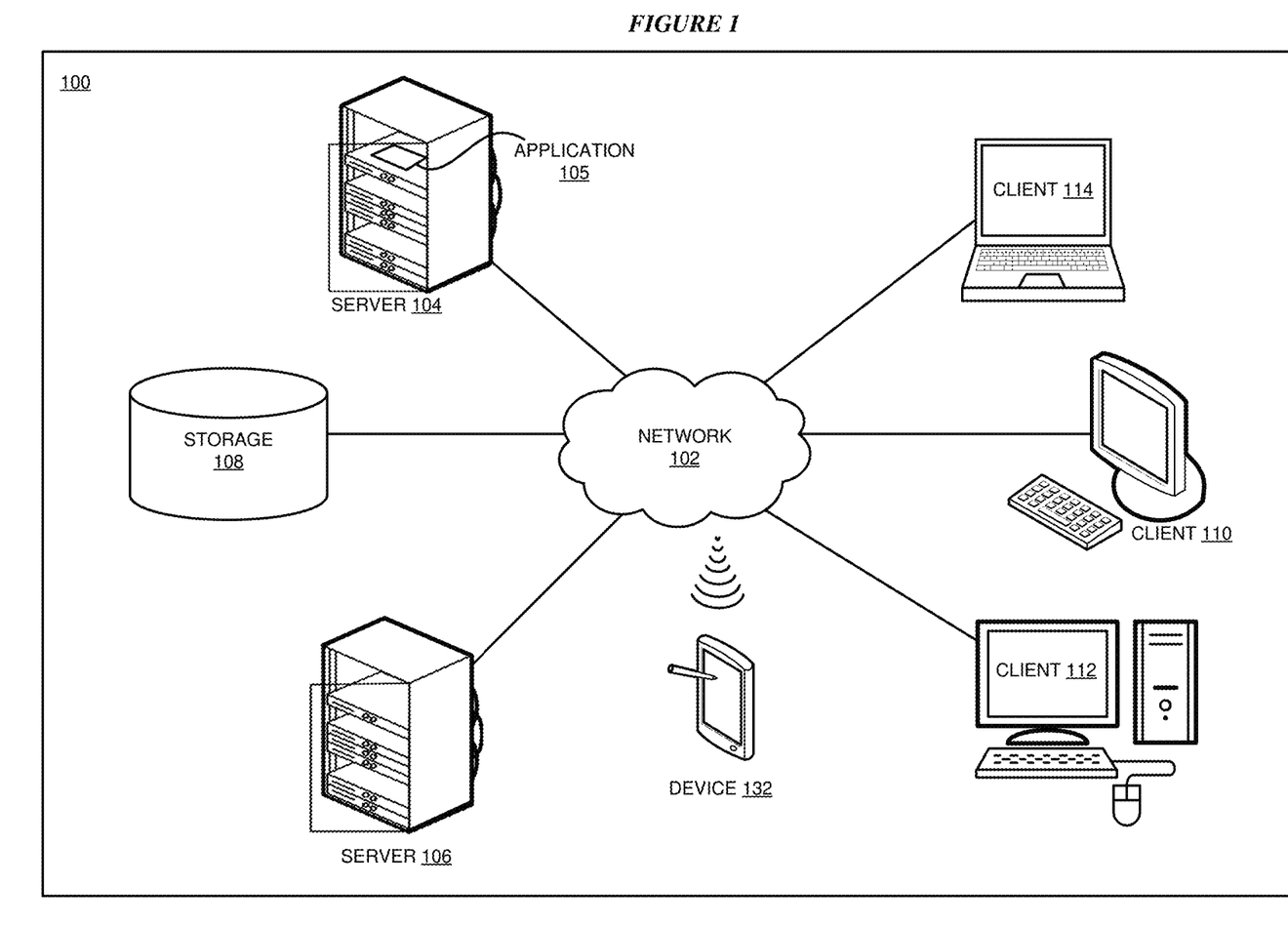
FIG. 1 depicts a block diagram of a network of data processing systems in which illustrative embodiments may be implemented.
Figure 2:
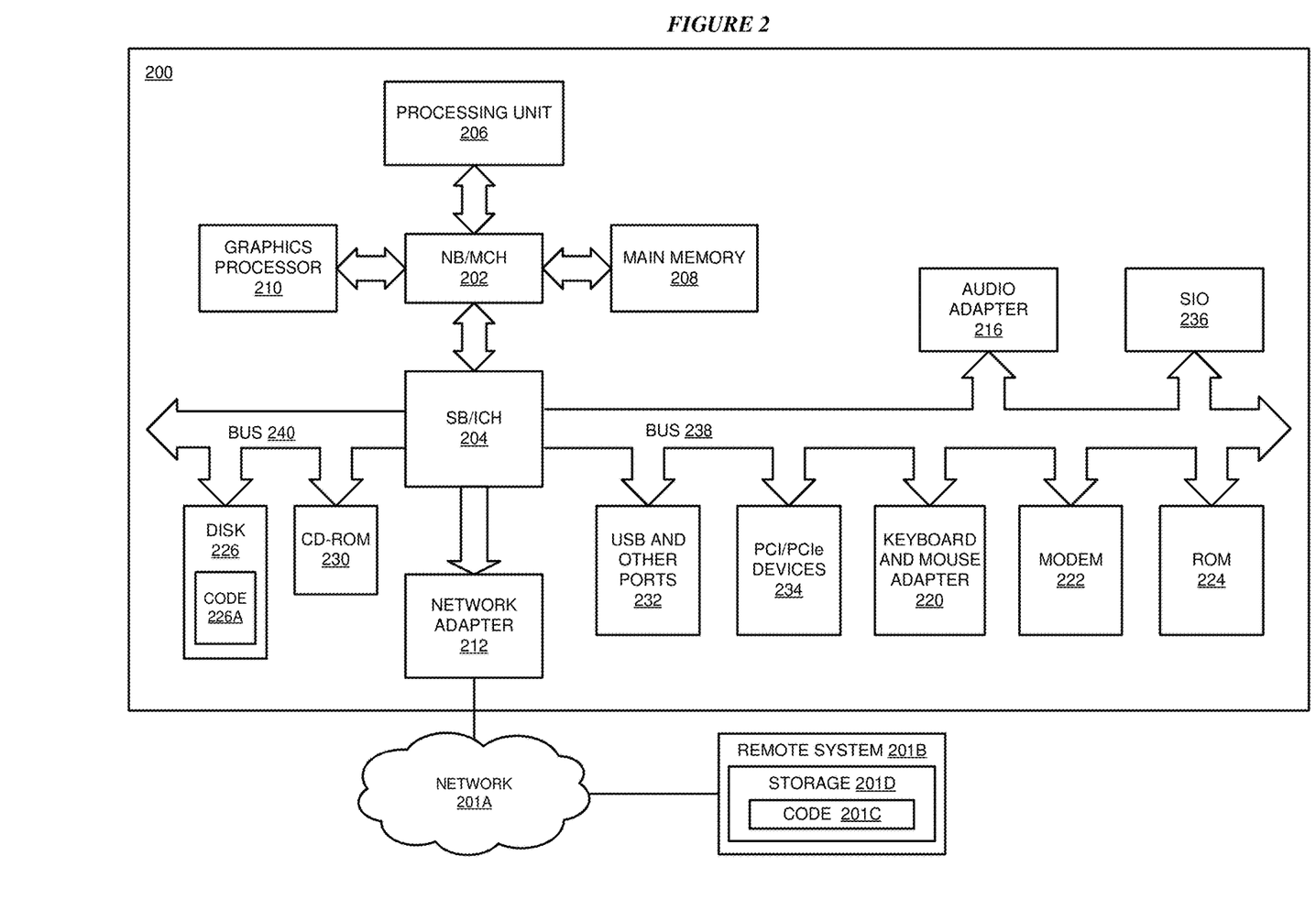
FIG. 2 depicts a block diagram of a data processing system in which illustrative embodiments may be implemented.

With reference to the figures and in particular with reference to FIGS. 1 and 2, these figures are example diagrams of data processing environments in which illustrative embodiments may be implemented. FIGS. 1 and 2 are only examples and are not intended to assert or imply any limitation with regard to the environments in which different embodiments may be implemented. A particular implementation may make many modifications to the depicted environments based on the following description.

FIG. 1 depicts a block diagram of a network of data processing systems in which illustrative embodiments may be implemented. Data processing environment 100 is a network of computers in which the illustrative embodiments may be implemented. Data processing environment 100 includes network 102. Network 102 is the medium used to provide communications links between various devices and computers connected together within data processing environment 100. Network 102 may include connections, such as wire, wireless communication links, or fiber optic cables.

Clients or servers are only example roles of certain data processing systems connected to network 102 and are not intended to exclude other configurations or roles for these data processing systems. Server 104 and server 106 couple to network 102 along with storage unit 108. Software applications may execute on any computer in data processing environment 100. Clients 110, 112, and 114 are also coupled to network 102. A data processing system, such as server 104 or 106, or client 110, 112, or 114 may contain data and may have software applications or software tools executing thereon.

Only as an example, and without implying any limitation to such architecture, FIG. 1 depicts certain components that are usable in an example implementation of an embodiment. For example, servers 104 and 106, and clients 110, 112, 114, are depicted as servers and clients only as example and not to imply a limitation to a client-server architecture. As another example, an embodiment can be distributed across several data processing systems and a data network as shown, whereas another embodiment can be implemented on a single data processing system within the scope of the illustrative embodiments. Data processing systems 104, 106, 110, 112, and 114 also represent example nodes in a cluster, partitions, and other configurations suitable for implementing an embodiment.

Device 132 is an example of a device described herein. For example, device 132 can take the form of a smartphone, a tablet computer, a laptop computer, client 110 in a stationary or a portable form, a wearable computing device, or any other suitable device. Any software application described as executing in another data processing system in FIG. 1 can be configured to execute in device 132 in a similar manner. Any data or information stored or produced in another data processing system in FIG. 1 can be configured to be stored or produced in device 132 in a similar manner.

Application 105 implements an embodiment described herein. Application 105 executes in any of servers 104 and 106, clients 110, 112, and 114, and device 132.

Servers 104 and 106, storage unit 108, and clients 110, 112, and 114, and device 132 may couple to network 102 using wired connections, wireless communication protocols, or other suitable data connectivity. Clients 110, 112, and 114 may be, for example, personal computers or network computers.

In the depicted example, server 104 may provide data, such as boot files, operating system images, and applications to clients 110, 112, and 114. Clients 110, 112, and 114 may be clients to server 104 in this example. Clients 110, 112, 114, or some combination thereof, may include their own data, boot files, operating system images, and applications. Data processing environment 100 may include additional servers, clients, and other devices that are not shown.

In the depicted example, data processing environment 100 may be the Internet. Network 102 may represent a collection of networks and gateways that use the Transmission Control Protocol/Internet Protocol (TCP/IP) and other protocols to communicate with one another. At the heart of the Internet is a backbone of data communication links between major nodes or host computers, including thousands of commercial, governmental, educational, and other computer systems that route data and messages. Of course, data processing environment 100 also may be implemented as a number of different types of networks, such as for example, an intranet, a local area network (LAN), or a wide area network (WAN). FIG. 1 is intended as an example, and not as an architectural limitation for the different illustrative embodiments.

Among other uses, data processing environment 100 may be used for implementing a client-server environment in which the illustrative embodiments may be implemented. A client-server environment enables software applications and data to be distributed across a network such that an application functions by using the interactivity between a client data processing system and a server data processing system. Data processing environment 100 may also employ a service oriented architecture where interoperable software components distributed across a network may be packaged together as coherent business applications. Data processing environment 100 may also take the form of a cloud, and employ a cloud computing model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service.

With reference to FIG. 2, this figure depicts a block diagram of a data processing system in which illustrative embodiments may be implemented. Data processing system 200 is an example of a computer, such as servers 104 and 106, or clients 110, 112, and 114 in FIG. 1, or another type of device in which computer usable program code or instructions implementing the processes may be located for the illustrative embodiments.

Data processing system 200 is also representative of a data processing system or a configuration therein, such as data processing system 132 in FIG. 1 in which computer usable program code or instructions implementing the processes of the illustrative embodiments may be located. Data processing system 200 is described as a computer only as an example, without being limited thereto. Implementations in the form of other devices, such as device 132 in FIG. 1, may modify data processing system 200, such as by adding a touch interface, and even eliminate certain depicted components from data processing system 200 without departing from the general description of the operations and functions of data processing system 200 described herein.

In the depicted example, data processing system 200 employs a hub architecture including North Bridge and memory controller hub (NB/MCH) 202 and South Bridge and input/output (I/O) controller hub (SB/ICH) 204. Processing unit 206, main memory 208, and graphics processor 210 are coupled to North Bridge and memory controller hub (NB/MCH) 202. Processing unit 206 may contain one or more processors and may be implemented using one or more heterogeneous processor systems. Processing unit 206 may be a multi-core processor. Graphics processor 210 may be coupled to NB/MCH 202 through an accelerated graphics port (AGP) in certain implementations.

In the depicted example, local area network (LAN) adapter 212 is coupled to South Bridge and I/O controller hub (SB/ICH) 204. Audio adapter 216, keyboard and mouse adapter 220, modem 222, read only memory (ROM) 224, universal serial bus (USB) and other ports 232, and PCI/PCIe devices 234 are coupled to South Bridge and I/O controller hub 204 through bus 238. Hard disk drive (HDD) or solid-state drive (SSD) 226 and CD-ROM 230 are coupled to South Bridge and I/O controller hub 204 through bus 240. PCI/PCIe devices 234 may include, for example, Ethernet adapters, add-in cards, and PC cards for notebook computers. PCI uses a card bus controller, while PCIe does not. ROM 224 may be, for example, a flash binary input/output system (BIOS). Hard disk drive 226 and CD-ROM 230 may use, for example, an integrated drive electronics (IDE), serial advanced technology attachment (SATA) interface, or variants such as external-SATA (eSATA) and micro-SATA (mSATA). A super I/O (SIO) device 236 may be coupled to South Bridge and I/O controller hub (SB/ICH) 204 through bus 238.

Memories, such as main memory 208, ROM 224, or flash memory (not shown), are some examples of computer usable storage devices. Hard disk drive or solid state drive 226, CD-ROM 230, and other similarly usable devices are some examples of computer usable storage devices including a computer usable storage medium.

An operating system runs on processing unit 206. The operating system coordinates and provides control of various components within data processing system 200 in FIG. 2. The operating system may be a commercially available operating system for any type of computing platform, including but not limited to server systems, personal computers, and mobile devices. An object oriented or other type of programming system may operate in conjunction with the operating system and provide calls to the operating system from programs or applications executing on data processing system 200.

Instructions for the operating system, the object-oriented programming system, and applications or programs, such as application 105 in FIG. 1, are located on storage devices, such as in the form of code 226A on hard disk drive 226, and may be loaded into at least one of one or more memories, such as main memory 208, for execution by processing unit 206. The processes of the illustrative embodiments may be performed by processing unit 206 using computer implemented instructions, which may be located in a memory, such as, for example, main memory 208, read only memory 224, or in one or more peripheral devices.

Furthermore, in one case, code 226A may be downloaded over network 201A from remote system 201B, where similar code 201C is stored on a storage device 201D. in another case, code 226A may be downloaded over network 201A to remote system 201B, where downloaded code 201C is stored on a storage device 201D.

The hardware in FIGS. 1-2 may vary depending on the implementation. Other internal hardware or peripheral devices, such as flash memory, equivalent non-volatile memory, or optical disk drives and the like, may be used in addition to or in place of the hardware depicted in FIGS. 1-2. In addition, the processes of the illustrative embodiments may be applied to a multiprocessor data processing system.

In some illustrative examples, data processing system 200 may be a personal digital assistant (PDA), which is generally configured with flash memory to provide non-volatile memory for storing operating system files and/or user-generated data. A bus system may comprise one or more buses, such as a system bus, an I/O bus, and a PCI bus. Of course, the bus system may be implemented using any type of communications fabric or architecture that provides for a transfer of data between different components or devices attached to the fabric or architecture.

A communications unit may include one or more devices used to transmit and receive data, such as a modem or a network adapter. A memory may be, for example, main memory 208 or a cache, such as the cache found in North Bridge and memory controller hub 202. A processing unit may include one or more processors or CPUs.

The depicted examples in FIGS. 1-2 and above-described examples are not meant to imply architectural limitations. For example, data processing system 200 also may be a tablet computer, laptop computer, or telephone device in addition to taking the form of a mobile or wearable device.

Where a computer or data processing system is described as a virtual machine, a virtual device, or a virtual component, the virtual machine, virtual device, or the virtual component operates in the manner of data processing system 200 using virtualized manifestation of some or all components depicted in data processing system 200. For example, in a virtual machine, virtual device, or virtual component, processing unit 206 is manifested as a virtualized instance of all or some number of hardware processing units 206 available in a host data processing system, main memory 208 is manifested as a virtualized instance of all or some portion of main memory 208 that may be available in the host data processing system, and disk 226 is manifested as a virtualized instance of all or some portion of disk 226 that may be available in the host data processing system. The host data processing system in such cases is represented by data processing system 200.

Figure 3:
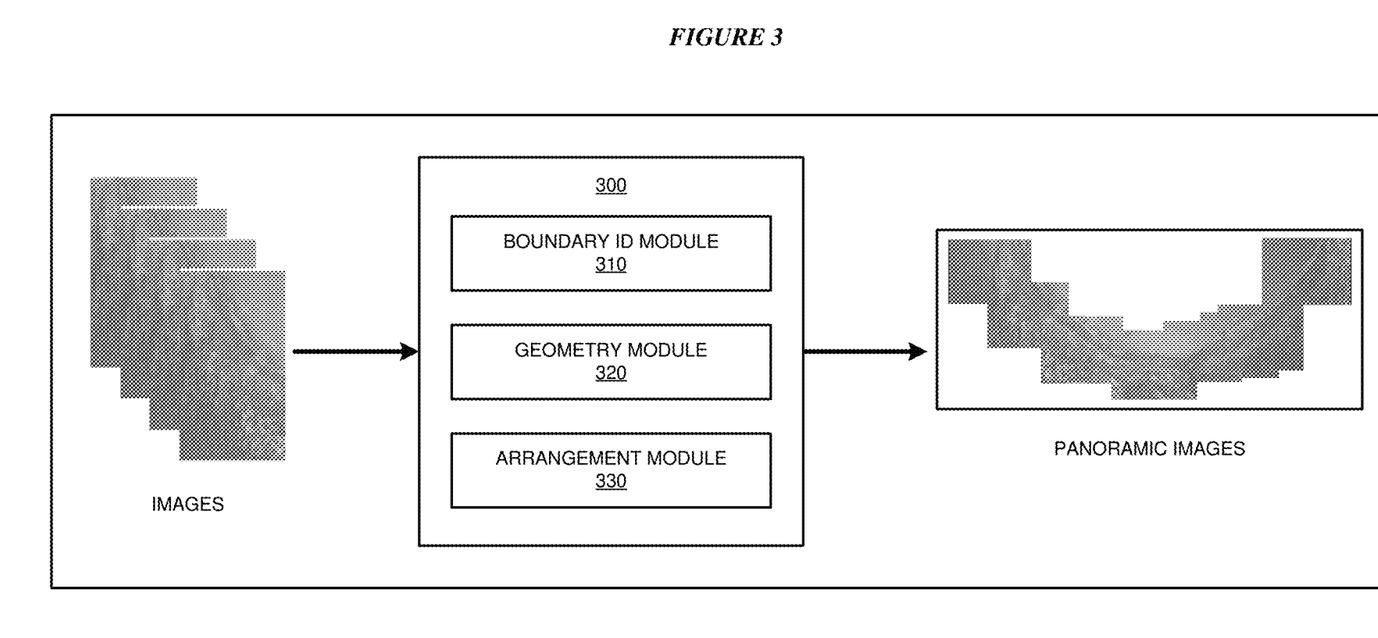
FIG. 3 depicts a block diagram of an example configuration for image stitching using geometry-based image orientation in accordance with an illustrative embodiment.

With reference to FIG. 3, this figure depicts a block diagram of an example configuration for image stitching using geometry-based image orientation in accordance with an illustrative embodiment. Application 300 is an example of application 105 in FIG. 1 and executes in any of servers 104 and 106, clients 110, 112, and 114, and device 132 in FIG. 1.

Boundary identification module 310 receives a set of source images of a subject or scene from which to form a panoramic image. The set of images is not required to be in any particular order. Images in the set of images may have been obtained individually or may be individual frames from a video segment. Module 310 identifies a boundary feature in a source image. To identify a boundary feature, module 310 uses a model trained to identify boundary features in images of a type the embodiment is configured to process. For example, an implementation of module 310 configured to process nail scan images uses an implementation of the U-Net network trained to identify boundary features in nail scan images.

Geometry module 320 treats an identified boundary feature within an image as a line segment, and selects a set of points within the line segment. One implementation of module 320 selects three points, at 10 percent, fifty percent, and ninety percent of the length of the line segment. Module 320 determines a set of parameters for a geometrical shape that includes the identified points within a source image. In one implementation of module 320, the geometrical shape is a circle, and for each selected point with coordinates x and y in the source image module 320 calculates center coordinates $x_0$ and $y_0$ and a radius r of the circle defined by the expression $(x-x_0)^2+(y-y_0)^2=r^2$. Module 320 then averages all the radii.

Modules 310 and 320 perform the boundary feature identification, point selection, and parameter determination for additional images in the set of source images, averaging the parameters, thus fitting an identified boundary feature within multiple source images to a common geometrical shape.

Arrangement module 330 uses the determined parameters of the common geometrical shape to arrange images in the set of source images in positions along the geometrical shape. For an implementation of module 330 using a circle as the common geometrical shape, module 330 calculates a phase for each identified point within an image. The phase represents a distance around the arc of the circle from a starting point. Module 330 uses the calculated phases in images in the set of source images to position the source images appropriately. Module 330 forms a panoramic image by combining the positioned source images, using any suitable technique and resolving overlap regions according to a configuration of module 330 in a manner described herein.

Figure 4:
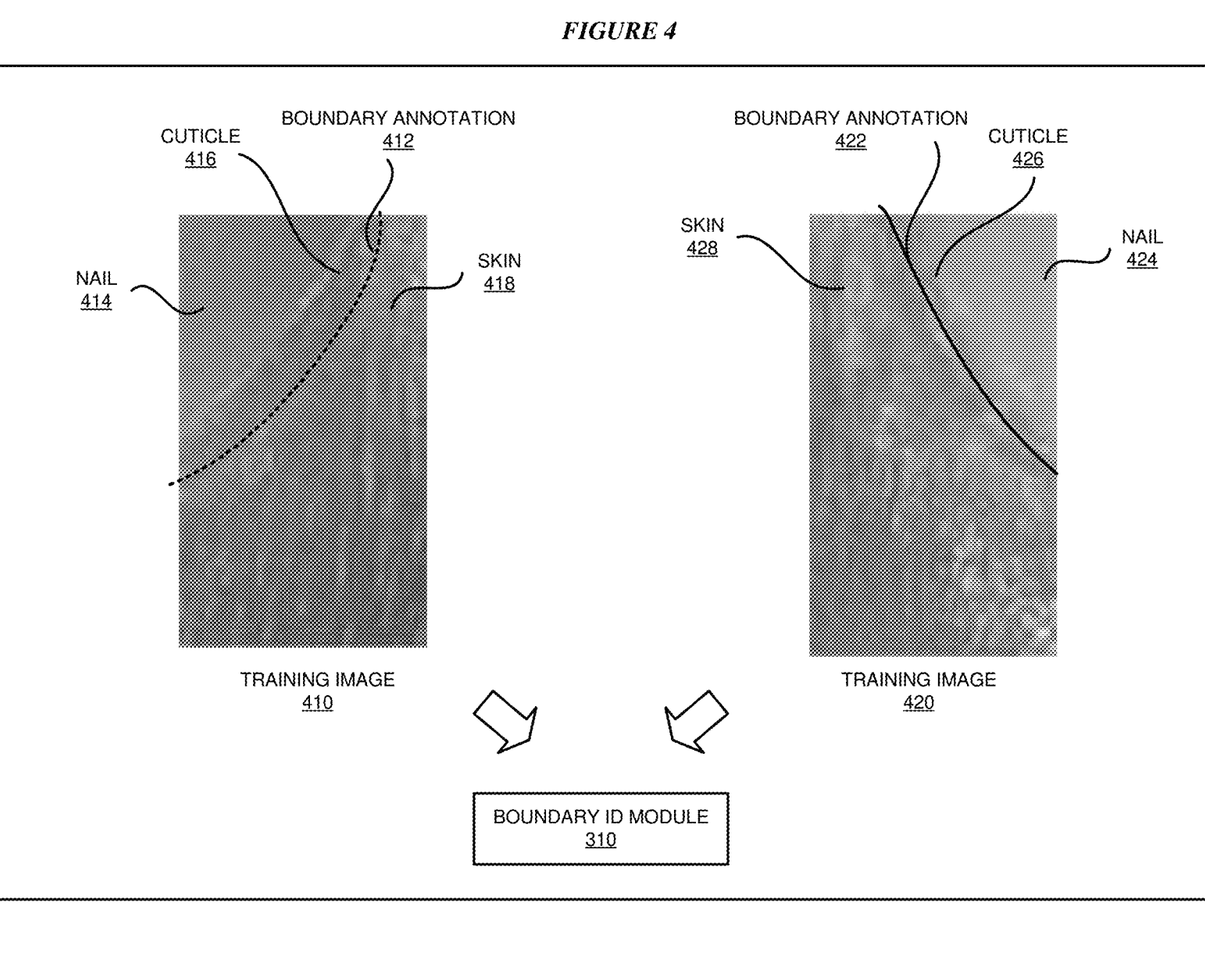
FIG. 4 depicts an example of use of training images in image stitching using geometry-based image orientation in accordance with an illustrative embodiment.

With reference to FIG. 4, this figure depicts an example of image stitching using geometry-based image orientation in accordance with an illustrative embodiment. The example can be executed using application 300 in FIG. 3. Boundary identification module 310 is the same as boundary identification module 310 in FIG. 3.

In particular, FIG. 4 depicts training images 410 and 420 for use in training boundary identification module 310 to identify a boundary feature in a nail scan image. Training images 410 and 420 are annotated nail scan images. Training image 410 includes boundary annotation 412 along cuticle 416, separating nail 414 from skin 418. Training image 420 includes boundary annotation 422 along cuticle 426, separating nail 424 from skin 428.

Figure 5:
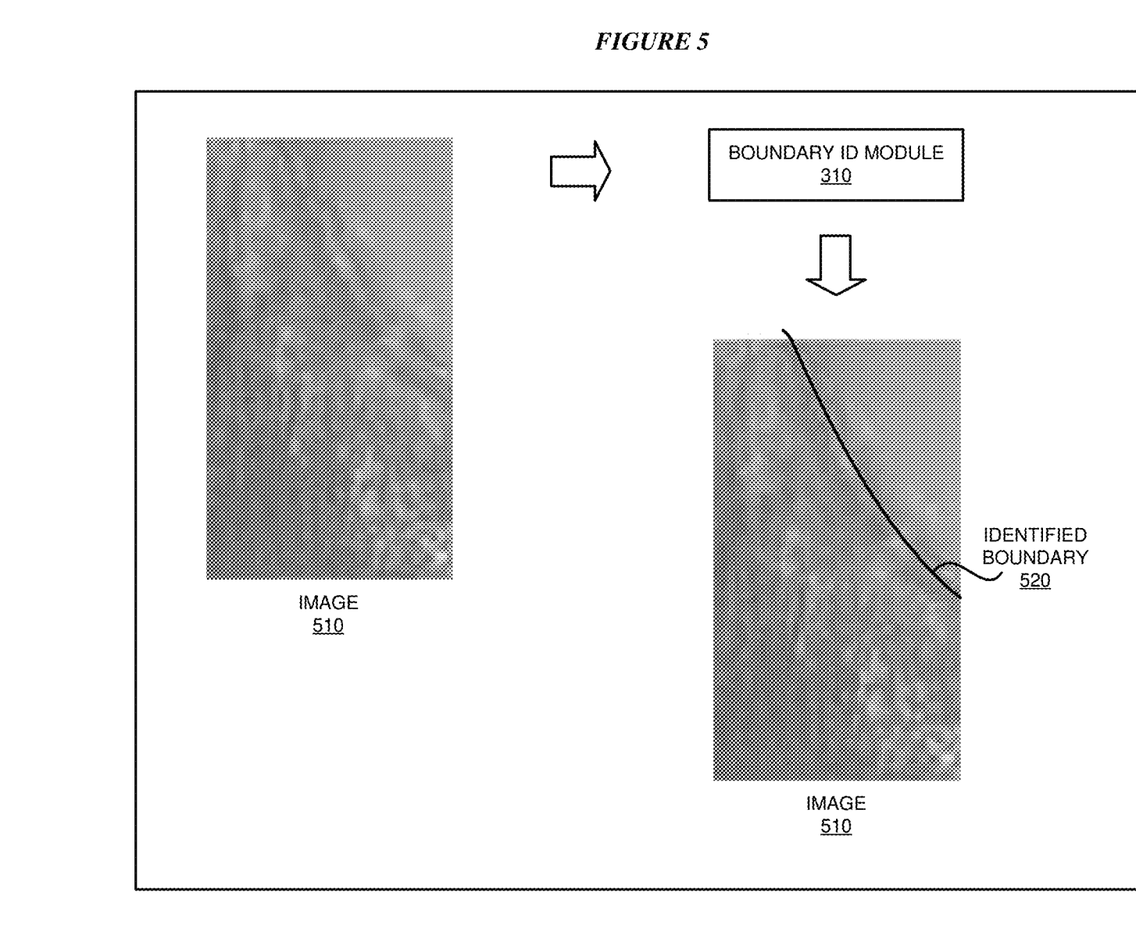
FIG. 5 depicts an example of image stitching using geometry-based image orientation in accordance with an illustrative embodiment.

With reference to FIG. 5, this figure depicts an example of image stitching using geometry-based image orientation in accordance with an illustrative embodiment. The example can be executed using application 300 in FIG. 3. Boundary identification module 310 is the same as boundary identification module 310 in FIG. 3.

In particular, FIG. 5 depicts the use of boundary identification module 310, once trained to identify a boundary feature in a nail scan image, on source image 510. Source image 510 is part of a set of source images to be assembled into a panoramic image. As depicted, boundary identification module 310 applies identified boundary 520 to image 510.

Figure 6:
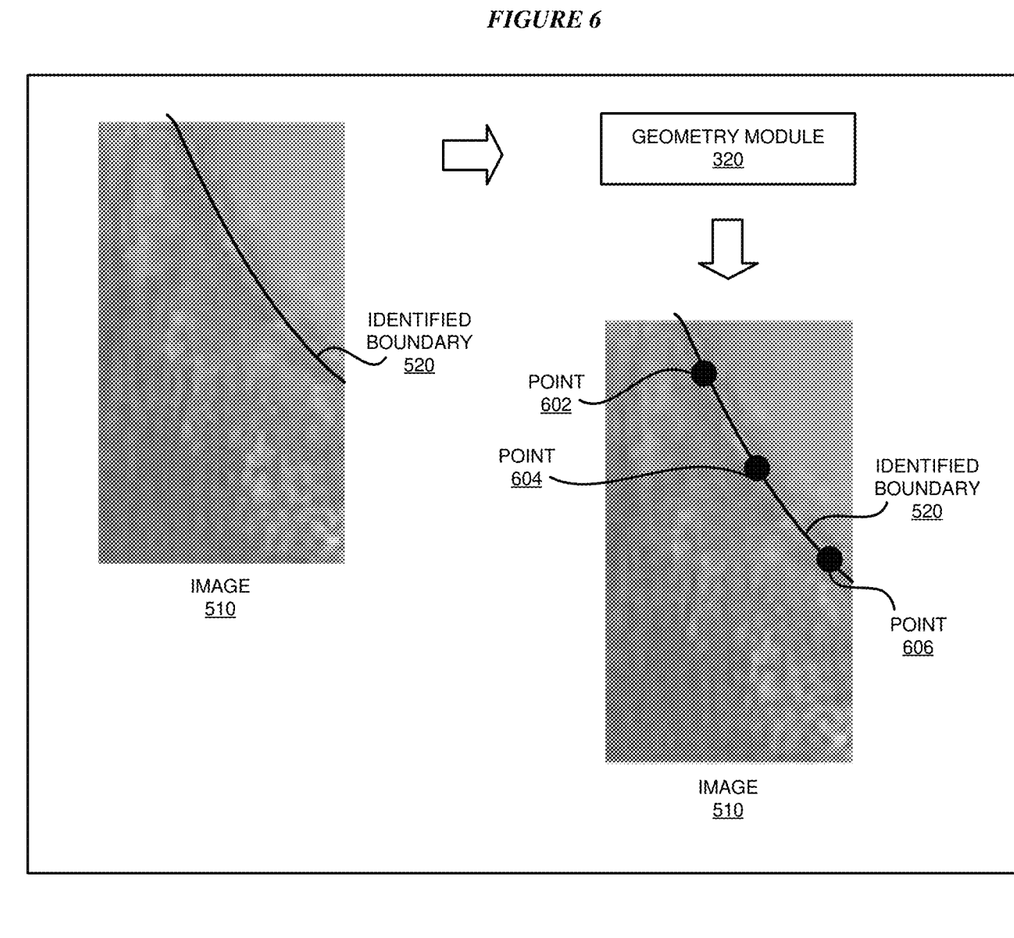
FIG. 6 depicts a continued example of image stitching using geometry-based image orientation in accordance with an illustrative embodiment.

With reference to FIG. 6, this figure depicts a continued example of image stitching using geometry-based image orientation in accordance with an illustrative embodiment. The example can be executed using application 300 in FIG.

3. Geometry module 320 is the same as geometry module 320 in FIG. 3. Image 510 and identified boundary 520 are the same as image 510 and identified boundary 520 in FIG. 5.

As depicted, module 320 has treated identified boundary 520 within image 510 as a line segment, and selected a set of points within boundary 520. Here, module 320 is configured to select points 602, 604, and 606, at ten percent, fifty percent, and ninety percent of the length of boundary 520 respectively.

Figure 7:
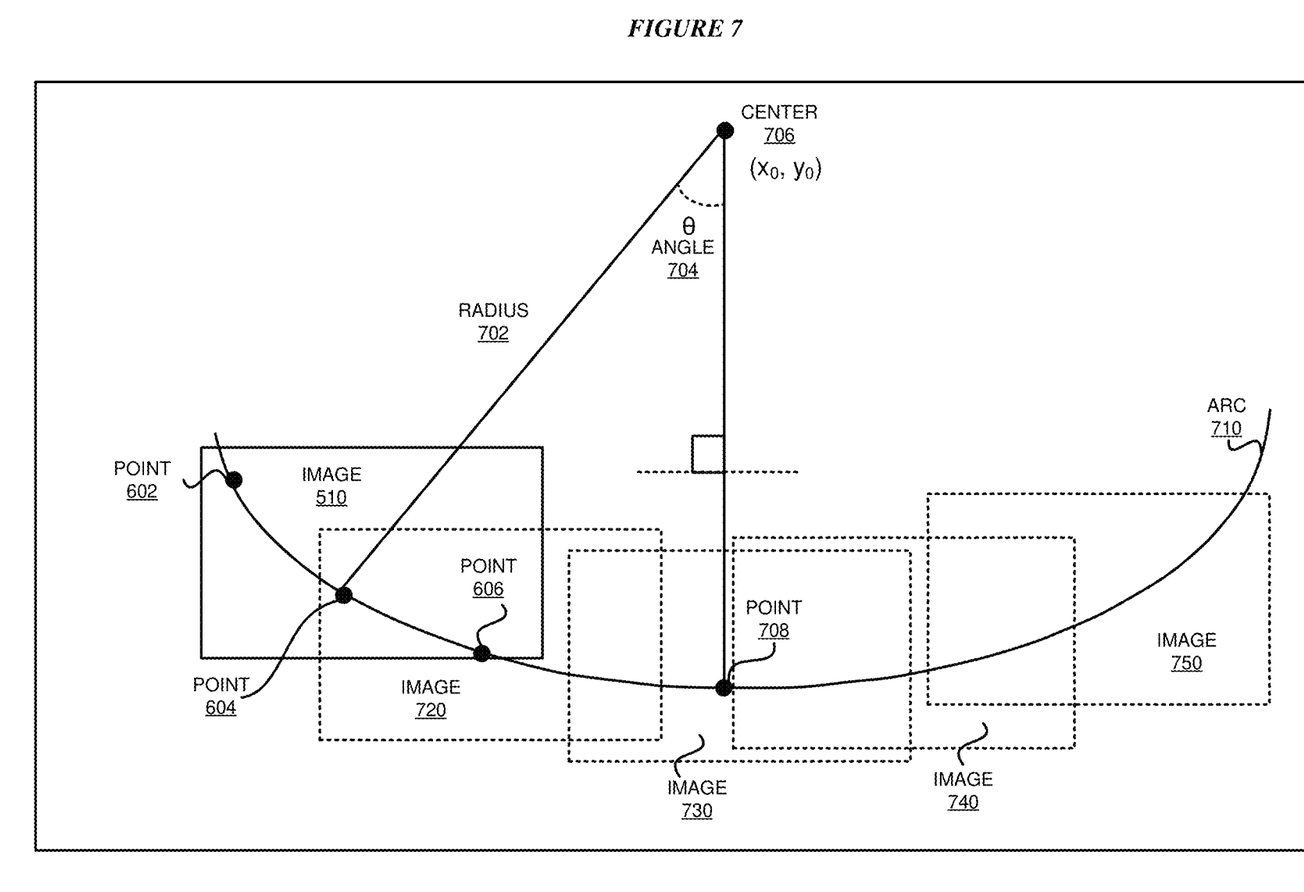
FIG. 7 depicts a further continued example of image stitching using geometry-based image orientation in accordance with an illustrative embodiment.

With reference to FIG. 7, this figure depicts a continued example of image stitching using geometry-based image orientation in accordance with an illustrative embodiment. The example can be executed using application 300 in FIG. 3. Image 510 and points 602, 604, and 606 are the same as image 510 and points 602, 604, and 606 in FIG. 6.

As depicted, application 300 has determined a set of parameters for a geometrical shape, a circle, that includes points 602, 604, and 606 within image 510. For each of points 602, 604, and 606, application 300 calculates center coordinates $x_0$ and $y_0$ at center 706 and radius (r) 702 of the circle defined by the expression $(x-x_0)^2+(y-y_0)^2=r^2$. The embodiment then averages all the radii to obtain radius 702. For each of images 510, 720, 730, 740, and 750, application 300 calculates a phase for each identified point within an image. The phase represents a distance around arc 710 from a starting point, point 708. Application 300 uses the calculated phases in images in the set of source images to position the source images appropriately. Here, as depicted, source image 510 includes points 602, 604, and 606 at −20, −15, and −10 degrees respectively. Source image 730 includes point 708 at 0 degrees, as well as other points not shown. Thus, image 730 belongs in the center of the resulting panoramic image, with image 510 at the left side as shown. Images 720, 730, 740, and 750 have also been placed along arc 710 according to phases of points within images 720, 730, 740, and 750 as shown.

Figure 8:
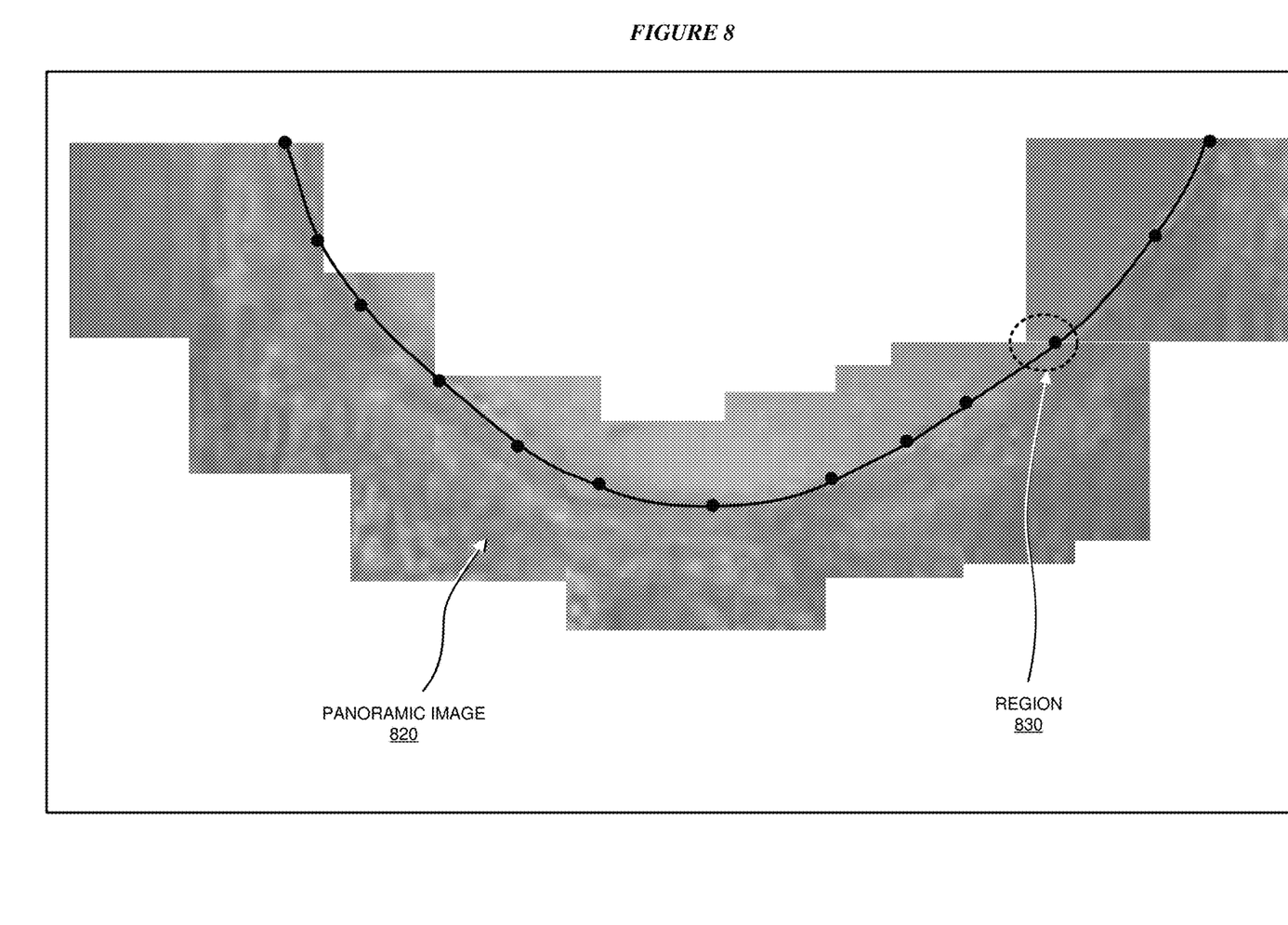
FIG. 8 depicts an additional example of image stitching using geometry-based image orientation in accordance with an illustrative embodiment.

With reference to FIG. 8, this figure depicts an example of image stitching using geometry-based image orientation in accordance with an illustrative embodiment. The example can be executed using application 300 in FIG. 3.

As depicted, a set of source images have been arranged into panoramic image 820 along a common geometrical shape. Of note, in region 830 application 300 has correctly placed the source images even though the source images do not overlap in this region.

Figure 9:
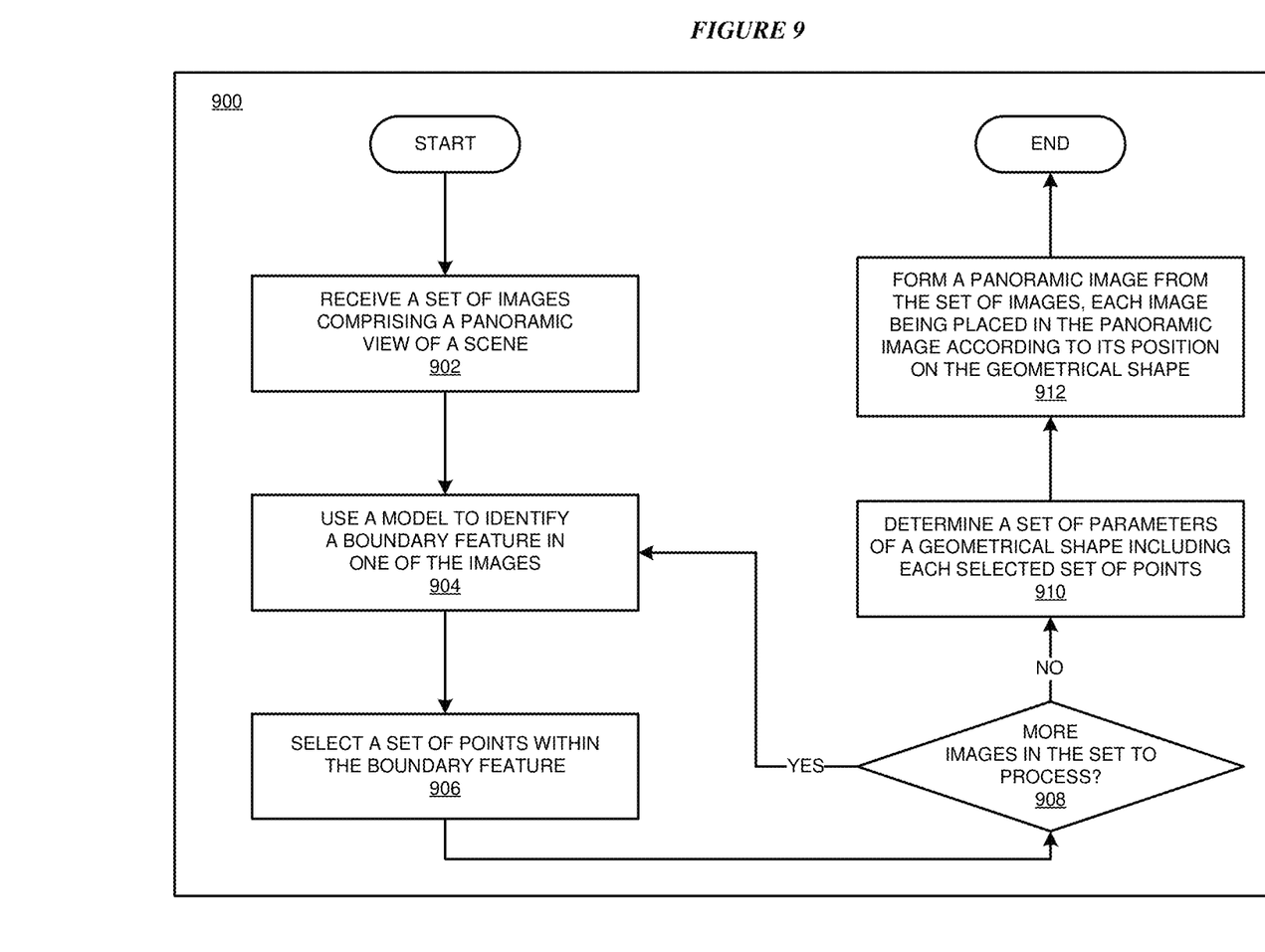
FIG. 9 depicts a flowchart of an example process for image stitching using geometry-based image orientation in accordance with an illustrative embodiment.

With reference to FIG. 9, this figure depicts a flowchart of an example process for image stitching using geometry-based image orientation in accordance with an illustrative embodiment. Process 900 can be implemented in application 300 in FIG. 3.

In block 902, the application receives a set of images comprising a panoramic view of a scene. In block 904, the application uses a model to identify a boundary feature in one of the images. In block 906, the application selects a set of points within the boundary feature. In block 908, the application determines whether there are more images in the set of images to process. If yes ("YES" path of block 908), the application returns to block 904. Otherwise ("NO" path of block 908), in block 910 the application determines a set of parameters of a geometrical shape including each selected set of points. In block 912, the application forms a panoramic image from the set of images, each image being placed in the panoramic image according to its position on the geometrical shape. Then the application ends.

Thus, a computer implemented method, system or apparatus, and computer program product are provided in the illustrative embodiments for image stitching using geometry-based image orientation and other related features, functions, or operations. Where an embodiment or a portion thereof is described with respect to a type of device, the computer implemented method, system or apparatus, the computer program product, or a portion thereof, are adapted or configured for use with a suitable and comparable manifestation of that type of device.

Where an embodiment is described as implemented in an application, the delivery of the application in a Software as a Service (SaaS) model is contemplated within the scope of the illustrative embodiments. In a SaaS model, the capability of the application implementing an embodiment is provided to a user by executing the application in a cloud infrastructure. The user can access the application using a variety of client devices through a thin client interface such as a web browser (e.g., web-based e-mail), or other light-weight client-applications. The user does not manage or control the underlying cloud infrastructure including the network, servers, operating systems, or the storage of the cloud infrastructure. In some cases, the user may not even manage or control the capabilities of the SaaS application. In some other cases, the SaaS implementation of the application may permit a possible exception of limited user-specific application configuration settings.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method comprising:
identifying, using a boundary identification model, a first boundary feature within a first image in a set of images, the first boundary feature comprising a first linear demarcation separating two areas in the first image, wherein different images in the set of images comprise respectively different portions of a scene;
selecting, within the first boundary feature, a first set of points;
identifying, using the boundary identification model, a second boundary feature within a second image in the set of images, the second boundary feature comprising a second linear demarcation separating two areas in the second image;
selecting, within the second boundary feature, a second set of points;
determining a set of parameters of a circle, the circle including the first set of points and the second set of points; and
forming, from the first image and the second image, a section of a panoramic image of the scene, the forming comprising:
fitting the first set of points and the second set of points on the circle such that the first boundary feature and the second boundary feature form a smooth contour in the section of the panoramic image of the scene,
placing the first image within the section of the panoramic image of the scene according to a phase of a point in the first set of points on the circle, the phase of the point in the first set of points comprising a first distance along the circle from a starting point, and
placing the second image in the section of the panoramic image of the scene according to a phase of a point in the second set of points on the circle, the phase of the point in the second set of points comprising a second distance along the circle from the starting point.

2. The computer-implemented method of claim 1, further comprising:
training, using a set of training images, the boundary identification model, an image in the set of training images comprising an annotated boundary feature.

3. The computer-implemented method of claim 1, wherein the first image and the second image comprise non-overlapping portions of the scene.

4. The computer-implemented method of claim 1, wherein the set of images is arranged randomly.

5. The computer-implemented method of claim 1, wherein the first set of points comprises three points evenly spaced along the first boundary feature.

6. A computer usable program product comprising one or more computer-readable storage devices, and program instructions stored on at least one of the one or more storage devices, the stored program instructions comprising:

program instructions to identify, using a boundary identification model, a first boundary feature within a first image in a set of images, the first boundary feature comprising a first linear demarcation separating two areas in the first image, wherein different images in the set of images comprise respectively different portions of a scene;

program instructions to select, within the first boundary feature, a first set of points;

program instructions to identify, using the boundary identification model, a second boundary feature within a second image in the set of images, the second boundary feature comprising a second linear demarcation separating two areas in the second image;

program instructions to select, within the second boundary feature, a second set of points;

program instructions to determine a set of parameters of a circle, the circle including the first set of points and the second set of points; and program instructions to form, from the first image and the second image, a section of a panoramic image of the scene, the program instructions to form comprising:

program instructions to fit the first set of points and the second set of points on the circle such that the first boundary feature and the second boundary feature form a smooth contour in the section of the panoramic image of the scene, program instructions to place the first image within the section of the panoramic image of the scene according to a phase of a point in the first set of points on the circle, the phase of the point in the first set of points comprising a first distance along the circle from a starting point, and program instructions to place the second image in the section of the panoramic image of the scene according to a phase of a point in the second set of points on the circle, the phase of the point in the second set of points comprising a second distance along the circle from the starting point.

7. The computer usable program product of claim 6, further comprising:

program instructions to train, using a set of training images, the boundary identification model, an image in the set of training images comprising an annotated boundary feature.

8. The computer usable program product of claim 6, wherein the first image and the second image comprise non-overlapping portions of the scene.

9. The computer usable program product of claim 6, wherein the set of images is arranged randomly.

10. The computer usable program product of claim 6, wherein the first set of points comprises three points evenly spaced along the first boundary feature.

11. The computer usable program product of claim 6, wherein the stored program instructions are stored in the at least one of the one or more storage devices of a local data processing system, and wherein the stored program instructions are transferred over a network from a remote data processing system.

12. The computer usable program product of claim 6, wherein the stored program instructions are stored in the at least one of the one or more storage devices of a server data processing system, and wherein the stored program instructions are downloaded over a network to a remote data processing system for use in a computer readable storage device associated with the remote data processing system.

13. A computer system comprising one or more processors, one or more computer-readable memories, and one or more computer-readable storage devices, and program instructions stored on at least one of the one or more storage devices for execution by at least one of the one or more processors via at least one of the one or more memories, the stored program instructions comprising:

program instructions to identify, using a boundary identification model, a first boundary feature within a first image in a set of images, the first boundary feature comprising a first linear demarcation separating two areas in the first image, wherein different images in the set of images comprise respectively different portions of a scene;

program instructions to select, within the first boundary feature, a first set of points;

program instructions to identify, using the boundary identification model, a second boundary feature within a second image in the set of images, the second boundary feature comprising a second linear demarcation separating two areas in the second image;

program instructions to select, within the second boundary feature, a second set of points;

program instructions to determine a set of parameters of a circle, the circle including the first set of points and the second set of points; and program instructions to form, from the first image and the second image, a section of a panoramic image of the scene, the program instructions to form comprising:

program instructions to fit the first set of points and the second set of points on the circle such that the first boundary feature and the second boundary feature form a smooth contour in the section of the panoramic image of the scene, program instructions to place the first image within the section of the panoramic image of the scene according to a phase of a point in the first set of points on the circle, the phase of the point in the first set of points comprising a first distance along the circle from a starting point, and program instructions to place the second image in the section of the panoramic image of the scene according to a phase of a point in the second set of points on the circle, the phase of the point in the second set of points comprising a second distance along the circle from the starting point.

14. The computer system of claim 13, further comprising:

program instructions to train, using a set of training images, the boundary identification model, an image in the set of training images comprising an annotated boundary feature.

15. The computer system of claim 13, wherein the first image and the second image comprise non-overlapping portions of the scene.

16. The computer system of claim 13, wherein the set of images is arranged randomly.

17. The computer system of claim 13, wherein the first set of points comprises three points evenly spaced along the first boundary feature.

\* \* \* \* \*